(12) United States Patent
Kagenow et al.

(10) Patent No.: US 8,199,189 B2
(45) Date of Patent: Jun. 12, 2012

(54) VEIN NAVIGATION DEVICE

(75) Inventors: Lise Kagenow, Oxford (GB); Morten Thing, Farum (DK)

(73) Assignee: Novarix Ltd. (GB)

( * ) Notice: Subject to any disclaimer, the term of this patent is extended or adjusted under 35 U.S.C. 154(b) by 385 days.

(21) Appl. No.: 12/295,632

(22) PCT Filed: Apr. 3, 2007

(86) PCT No.: PCT/DK2007/000170
§ 371 (c)(1),
(2), (4) Date: Mar. 24, 2010

(87) PCT Pub. No.: WO2007/115570
PCT Pub. Date: Oct. 18, 2007

(65) Prior Publication Data
US 2010/0177182 A1    Jul. 15, 2010

(30) Foreign Application Priority Data

Apr. 7, 2006 (DK) ................................ 2006 00505
Dec. 22, 2006 (DK) ................................ 2006 01697

(51) Int. Cl.
*H04N 7/18* (2006.01)
(52) U.S. Cl. ............................................................ 348/77
(58) Field of Classification Search ................. 348/77; 604/510; 600/549, 473, 430; 424/423; 435/4
See application file for complete search history.

(56) References Cited

U.S. PATENT DOCUMENTS

| | | | |
|---|---|---|---|
| 4,407,292 A * | 10/1983 | Edrich | 600/430 |
| 4,619,249 A | 10/1986 | Landry et al. | |
| 4,817,622 A | 4/1989 | Pennypacker et al. | |
| 5,146,923 A | 9/1992 | Dhawan | |
| 5,519,208 A | 5/1996 | Esparza et al. | |
| 5,608,210 A | 3/1997 | Esparza et al. | |
| 5,876,346 A | 3/1999 | Corso | |
| 5,947,906 A | 9/1999 | Dawson, Jr. et al. | |
| 5,954,701 A | 9/1999 | Matalon et al. | |
| 5,983,120 A | 11/1999 | Groner et al. | |
| 6,068,599 A | 5/2000 | Saito et al. | |
| 6,104,939 A | 8/2000 | Groner et al. | |
| 6,177,984 B1 | 1/2001 | Jacques | |

(Continued)

FOREIGN PATENT DOCUMENTS

CH     1439433     9/2003

(Continued)

OTHER PUBLICATIONS

Laser Surg Med, vol. 34, Issue 1; Vladimir P. Zharov et al; Infrared Imaging of Subcutaneous Veins, p. 56-61, published online Jan. 15, 2004.

(Continued)

*Primary Examiner* — Le H Luu

(74) *Attorney, Agent, or Firm* — Gifford, Krass, Sprinkle, Anderson & Citkowski, P.C.

(57) ABSTRACT

The present invention relates to an imaging device designed with the intent of visualizing subcutaneous structures within an organism. Visualization of subcutaneous structures will increase the speed and accuracy with which medical treatments requiring insertion of instruments into these structures can be performed. Especially fluid insertions into or extractions from an organism will be facilitated as the device is adapted to be placed upon the organism in a manner giving continued full mobility for the recipient and operator of the device.

27 Claims, 7 Drawing Sheets

U.S. PATENT DOCUMENTS

| | | |
|---|---|---|
| 6,178,340 B1 | 1/2001 | Svetliza et al. |
| 6,424,858 B1 | 7/2002 | Williams |
| 6,463,309 B1 | 10/2002 | Ilia et al. |
| 2003/0018271 A1* | 1/2003 | Kimble .......................... 600/473 |
| 2004/0015158 A1 | 1/2004 | Chen et al. |
| 2004/0111030 A1 | 6/2004 | Zeman |
| 2004/0215081 A1 | 10/2004 | Crane et al. |
| 2005/0119546 A9 | 6/2005 | Reynolds |
| 2005/0168980 A1 | 8/2005 | Dryden et al. |
| 2005/0221276 A1* | 10/2005 | Rozakis et al. ................ 435/4 |
| 2006/0020212 A1 | 1/2006 | Xu et al. |
| 2006/0122515 A1* | 6/2006 | Zeman et al. ................ 600/473 |
| 2006/0210603 A1* | 9/2006 | Williams et al. .............. 424/423 |
| 2007/0225614 A1* | 9/2007 | Naghavi et al. .............. 600/549 |
| 2009/0318891 A1* | 12/2009 | Marcotte et al. .............. 604/510 |

FOREIGN PATENT DOCUMENTS

| | | |
|---|---|---|
| CN | 1476810 | 2/2004 |
| CN | 1621889 | 6/2005 |
| EP | 1 447 044 | 8/2004 |
| EP | 1 527 735 | 5/2005 |
| EP | 1 743 570 | 1/2007 |
| GB | 2 364 376 | 1/2002 |
| GR | 1003158 | 6/1999 |
| JP | 2174854 | 7/1990 |
| JP | 7255847 | 10/1995 |
| JP | 2000316866 | 11/2000 |
| JP | 2004267534 | 9/2004 |
| JP | 2006 130201 | 5/2006 |
| WO | WO 93/16640 | 9/1993 |
| WO | WO 01/82786 | 11/2001 |
| WO | WO 02/064188 | 8/2002 |
| WO | WO 02/094093 | 11/2002 |
| WO | WO 2006/113748 | 10/2008 |

OTHER PUBLICATIONS

Watanabe et al., Palm vein authentication technology and its applications.

* cited by examiner

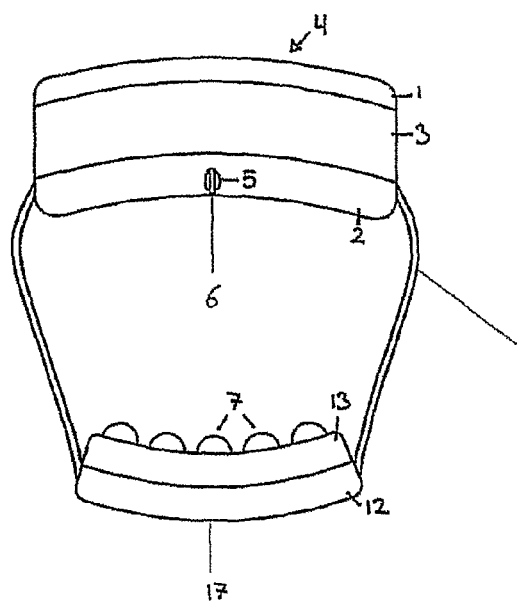
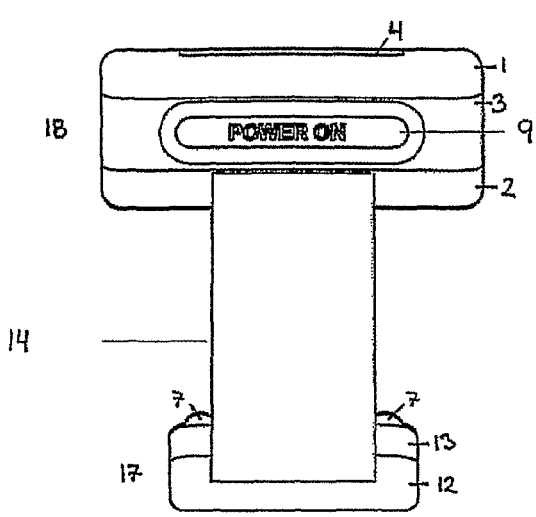
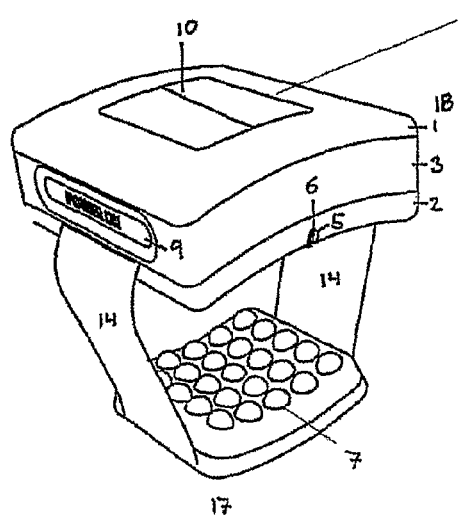
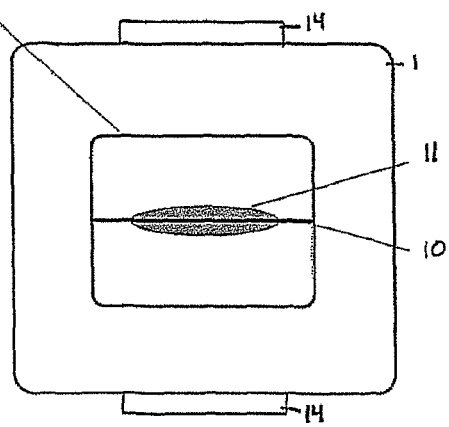
Fig. 2

3a
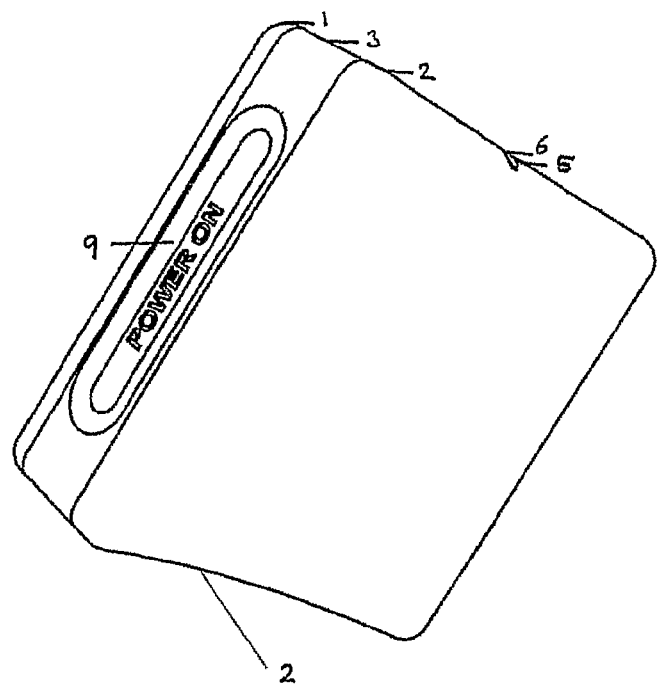
3b
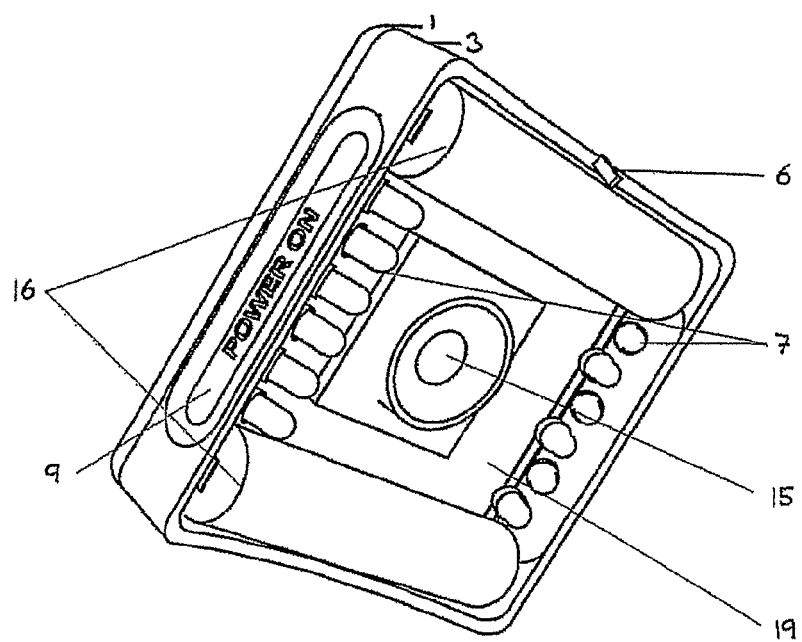
Fig 3

5a
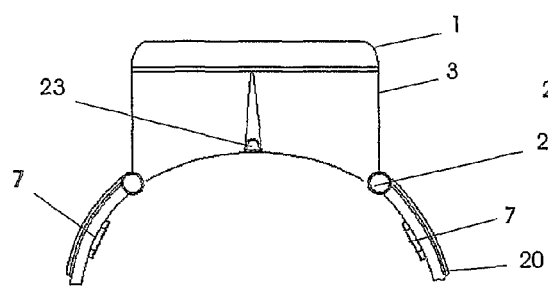
5b
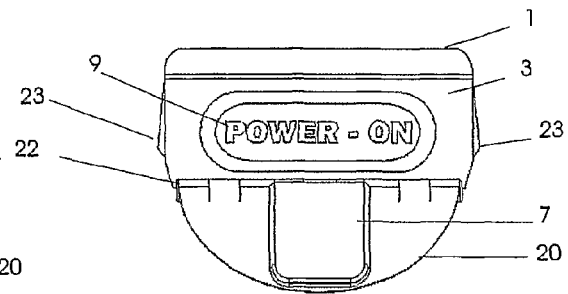
5c
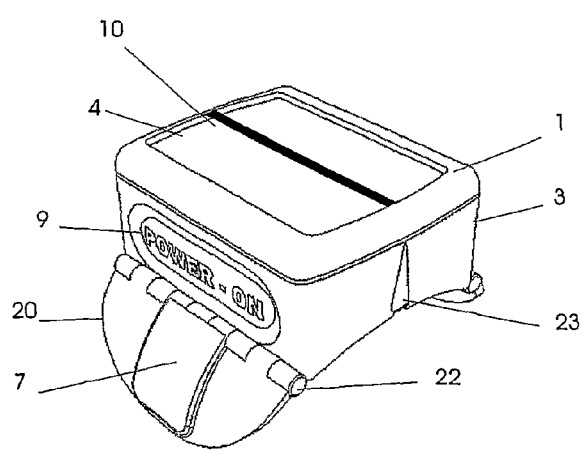
5d
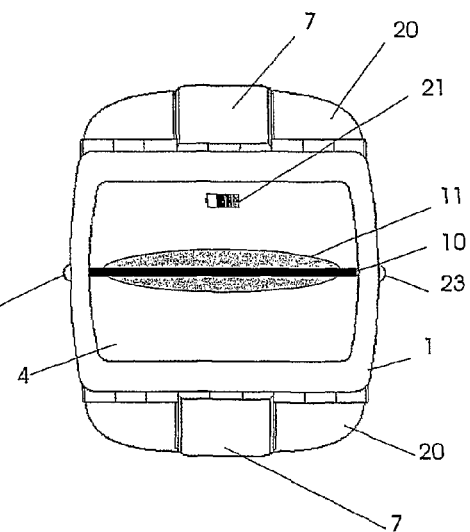
Fig. 5

6a
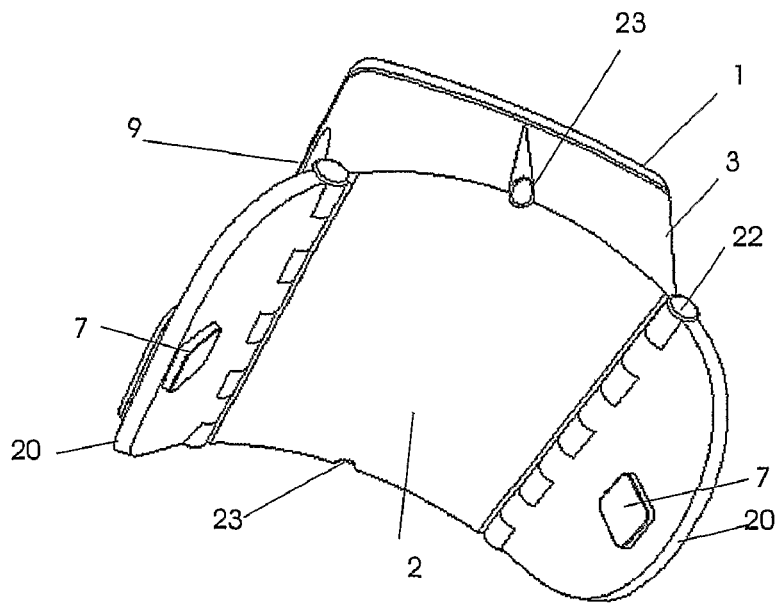
6b
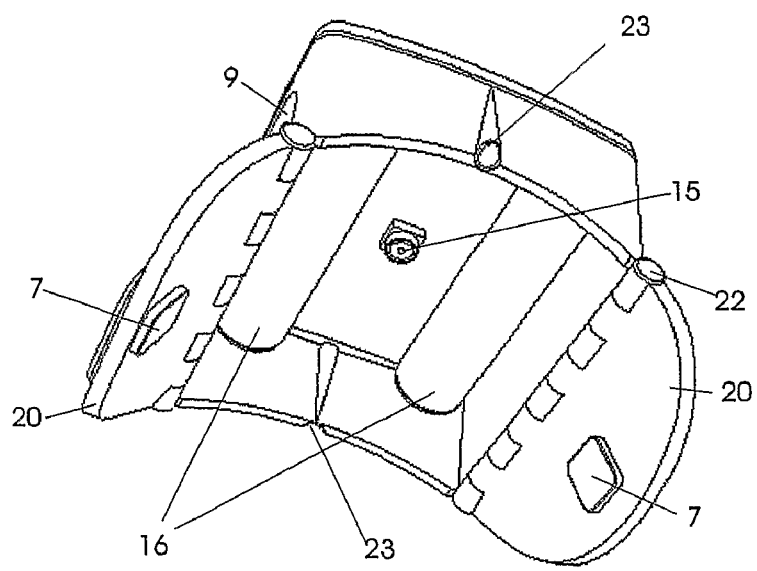
Fig 6

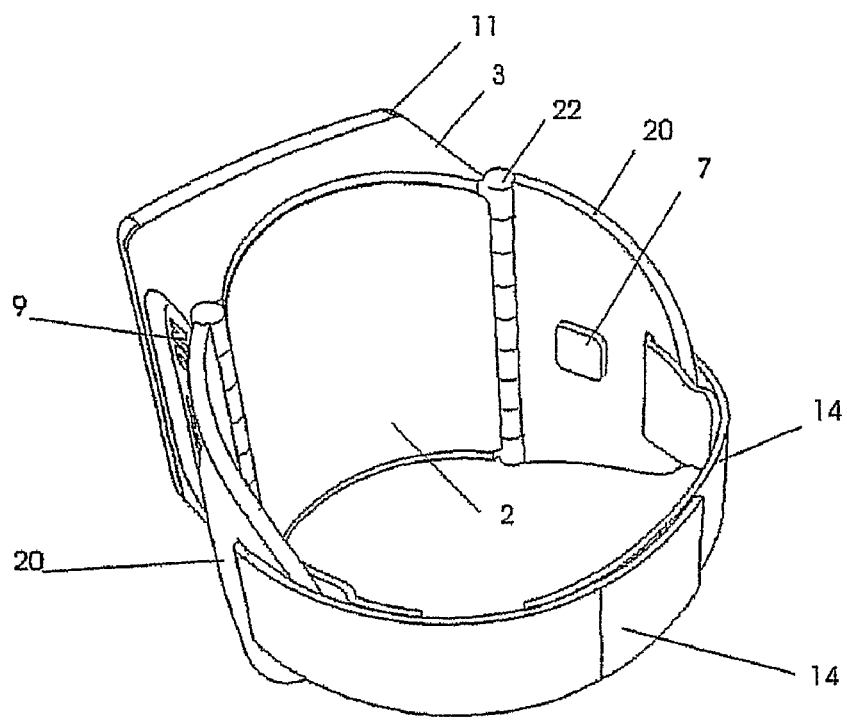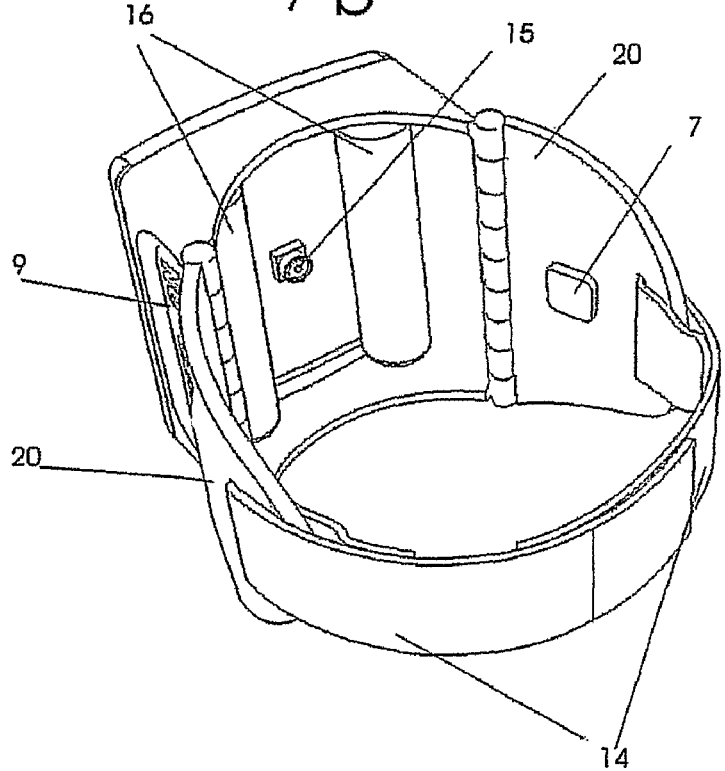
Fig 7

VEIN NAVIGATION DEVICE

All patent and non-patent references cited in the application, or in the present application, are also hereby incorporated by reference in their entirety.

FIELD OF INVENTION

The present invention relates to an imaging device and procedures for use of same for non-invasive visualization of subcutaneous structures within an organism. Visualization of subcutaneous structures will increase the speed and accuracy with which medical treatments requiring insertion of instruments into these structures can be performed. Especially fluid insertions into or extractions from an organism will be facilitated as the device is adapted to be placed upon the organism in a manner giving continued full mobility for the recipient and operator of the device.

BACKGROUND OF INVENTION

Several medical procedures necessitate puncture of subcutaneous blood vessels and therefore require the precise localization of these. Most commonly the localization is done visually or by palpitating the selected area, but this can be hampered if the recipient of the medical treatment has small, deep-lying vessels, is obese, is an infant, is anaemic, has a dark skin complexion, experiences vein contraction due to stress or suffers from burns, blood loss, dehydration or varicose veins. Vein wall thickening or scar tissue due to repeated treatment with venous access devices may also hamper cannulation procedures. Missing the vessel during injection can be unpleasant as this requires repeated stabbing, but can also have serious consequences such as extra vascular hemorrhaging if the vessel is punctured or tissue toxicity, if for example injecting chemotherapeutic agents.

Numerous inventions have been provided for localization of blood vessels in the prior art. In U.S. Pat. No. 5,608,210 Esparza describes an invention utilizing infrared light for aiding in locating a vein for insertion of a hypodermic needle. The operator performing the injection wears a headpiece which in front of one or both eyes comprises an infrared light source, a video camera and a monitor screen. This is unpractical and limits the mobility of the operator of the device.

In U.S. Pat. No. 6,178,340, the main technical components of the invention are the same as in the above mentioned invention. However, the components of the invention described in U.S. Pat. No. 6,178,340 are comprised within a frame and placed on a stand between the operator of the device and the recipient. The operator puts on two-color filter glasses to achieve a three dimensional effect of the generated image. Again, the requirement of eyewear is unpractical, and the use of a stand limits the flexibility and speed of the use of the device.

Reynolds describes in U.S. Pat. Appl. Pub. 2005/0119546 an invention which is placed directly upon the recipient. Although the invention includes light emitting diodes (LEDs) and a display, this invention does not provide the operator with a real time video image of the subcutaneous blood vessels and cannot display the insertion of, for example a hypodermic needle, into such a vessel.

There still exists a need for a small, practical, real time imaging system for visualizing subcutaneous blood filled structures which is intuitive in use, does not restrain the movements of either the operator of the device or the recipient of any medical treatment, which might benefit from the use of the device, and is usable in nearly any setting.

SUMMARY OF INVENTION

The present invention relates to a medical imaging device and procedures for use of same for visualization of subcutaneous structures by non-invasive means. The visualization will facilitate administering medical treatments requiring insertion of medical equipment into the subcutaneous structures. This is further facilitated by the device being adapted to be placed upon the recipient, leaving the operator of the device with both hands free and not restricting body movements for either operator or recipient of the treatment.

It is therefore an object of the present invention to provide an imaging device designed with the intent of visualizing subcutaneous structures in a body, where the device being adapted to be placed directly upon the recipient, comprises: at least one light emitting source illuminating a selected area of body surface, hereunder lying tissue and subcutaneous structures, at least one camera enabled detection system recording an image of said illuminated subcutaneous structures, and at least one display means rendering a recorded image of the illuminated subcutaneous structures.

It is yet an object of the present invention to provide use of a device adapted to be placed directly upon the recipient with the purpose of visualizing subcutaneous structures in a body, comprising the steps of: emitting light onto a selected area of body surface, hereunder lying tissue and subcutaneous structures, detecting the unabsorbed light by camera enabled detecting means and recording an image of illuminated subcutaneous structures and displaying the image of illuminated subcutaneous structures.

It is furthermore an object of the present invention to provide a method of visualizing subcutaneous structures in a body, with a device adapted to be placed directly upon the recipient comprising the steps of emitting light onto a selected area of body surface, hereunder lying tissue and subcutaneous structures, detecting the unabsorbed light by camera enabled detecting means and recording an image of illuminated subcutaneous structures and finally displaying the image of the illuminated subcutaneous structures.

DESCRIPTION OF DRAWINGS

FIG. 2: Illustrates a representative embodiment of the invention employing a trans-illuminating mode of illuminating and visualizing subcutaneous blood filled structures.

FIG. 3: Illustrates the underside and some of the internal components of a representative embodiment of the invention employing a reflective mode of illuminating and visualizing subcutaneous blood filled structures.

FIG. 5: Illustrates a preferred embodiment of the invention employing a reflective mode of illuminating and visualizing subcutaneous blood filled structures, this embodiment comprising symmetrical light guides.

FIG. 6: Illustrates the underside and some of the internal components of a preferred embodiment of the invention employing a reflective mode of illuminating and visualizing subcutaneous blood filled structures, this embodiment comprising symmetrical light guides.

FIG. 7: Illustrates the underside and some of the internal components of a preferred embodiment of the invention employing a reflective mode of illuminating and visualizing subcutaneous blood filled structures, this embodiment comprising straps.

DETAILED DESCRIPTION OF THE INVENTION

Figure 1:
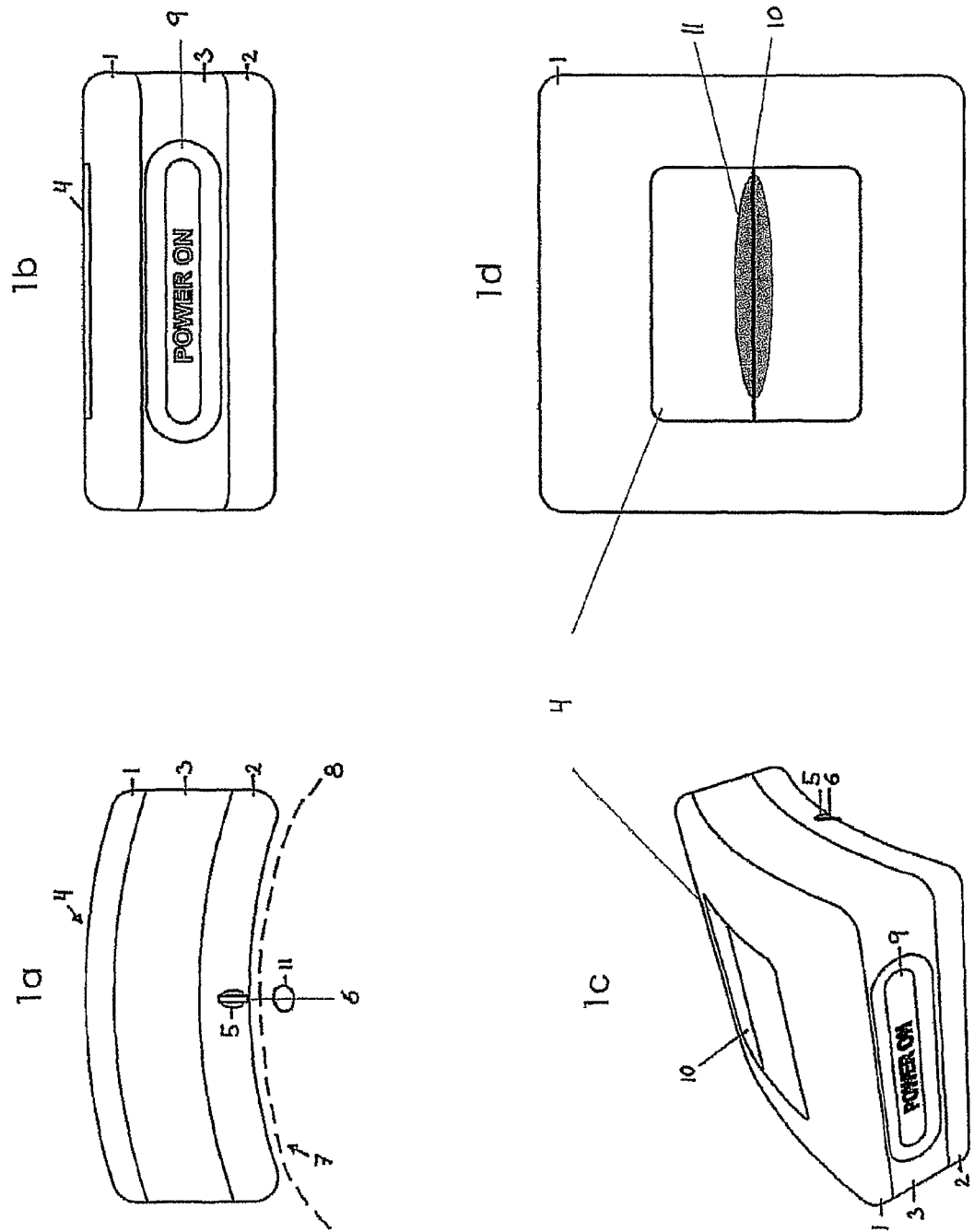
FIG. 1: Illustrates a representative embodiment of the invention employing a reflective mode of illuminating and visualizing subcutaneous blood filled structures.
Figure 4:
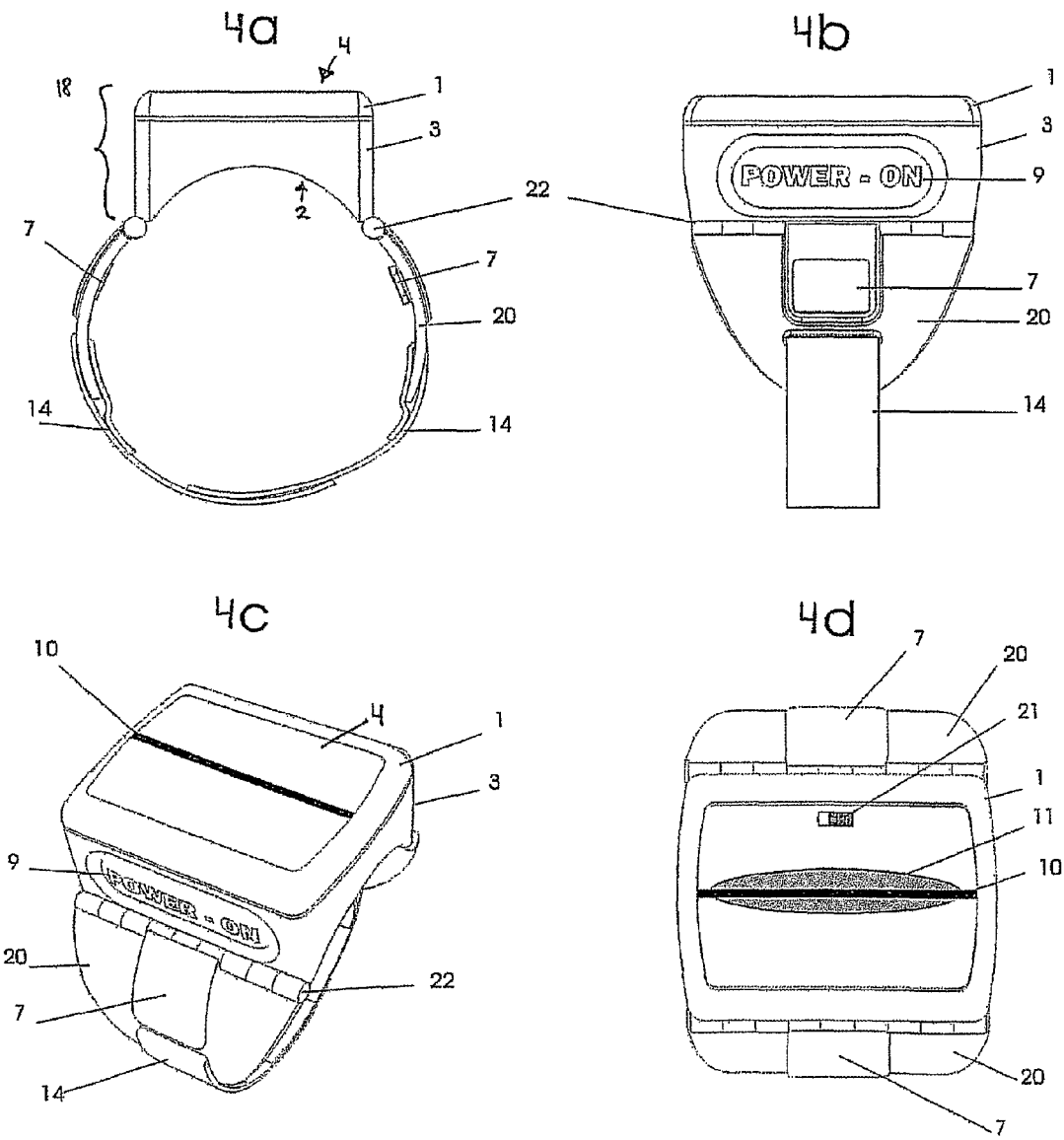
FIG. 4: Illustrates a preferred embodiment of the invention employing a reflective mode of illuminating and visualizing subcutaneous blood filled structures, this embodiment comprising straps.

The present invention relates to a device and use of same for real time visualization of subcutaneous structures for the purpose of facilitating the insertion of medical instruments e.g. hypodermic needles, into said subcutaneous structures. The invention comprises a light emitting source, a camera and a display and is adapted to be placed upon a recipient of a medical treatment.

Adaptation to Recipient

The invention has been adapted to be placed upon the recipient in several ways. Firstly, the device is small and lightweight and therefore does not cause undue strain upon the recipient. Secondly, a fastening means can be used in conjunction with the device. Thirdly, the device itself can be shaped to fit a certain anatomical part e.g. an arm or it can be flexible in its form.

The size of the device is less than 1000 cm$^3$. Preferably the device will be smaller than 500 cm$^3$, 400 cm$^3$ or 350 cm$^3$, more preferably smaller than 300 cm$^3$, 250 cm$^3$, 180 cm$^3$ or 125 cm$^3$, most preferably smaller than 100 cm$^3$ or 50 cm$^3$. The weight of the device will be no greater than 500 g; it may weigh less than 350 g, preferably less than 250 g, or less than 175 g, more preferably less than 100 g, or less than 90 g, most preferably less than 80 g, 70 g, 60 g or 50 g. It is more preferable to have a light weight device as the device is to be born by the recipient and thus the device is of less than 100 g of weight.

A fastening means can be used to secure the placement of the device upon the recipient. The fastening means can be an adhesive such as tape, double sided tape, glue or removable glue. These can all be products that are specially adapted for medical purposes to reduce the amount of irritation to the surface or skin of the recipient. The fastening means can be any kind of strap, belt, band, or elastic material of any material such as rubber, plastic, fabric or metal, and can be in a single unit to be slipped upon the recipient or be a two piece arrangement to be brought together by Velcro, tying, buckling, semi-permanent glue or the like. The fastening means can be a permanent feature of the present invention or it can be removable, such as detachable, for cleaning or hygienic purposes or it can be single use, such as a sleeve, wrap, cover, envelope or bag into which the device fits and which can be fastened to the recipient by tape or tying or other. The device may be fastened to the recipient with a single use cover, wrapper, strap, slip, pocket or the like any of which may stick to the cover, wrapper, strap, slip, pocket or the like itself or directly to the recipient by means of a low-tack, reusable or repositionable adhesive. The single use wrapper or the like can be of transparent plastic or rubber of any thickness and flexibility. Preferably, the device is contained within a single use cover.

It is an object of the present invention to provide a box or kit comprising the device, a number of single use wrappers, covers or the like and one or more sets of detachable straps. The number of single use covers may be any number over one, such as 10, 20, 30, 40, 50, 60, 75 or 100 covers or any number therein between or above. The kit may further comprise an instruction manual and or batteries. A separate box or kit of single use covers suitable for use with the device is also an object of the present invention.

The device itself can in a preferred embodiment be curved in a semicircular manner whereby the shape alone lets the device rest upon the recipient. The device can in an alternative embodiment be flexible by arranging the components of the device in a manner so that they are separable from one another or by the use of flexible components such as an organic display, which in itself is a bendable structure. The device can be partially flexible by having a lower part to be placed on the recipient that is made of a pliant and flexible material attached to an unalterable top part. The flexible material may adapt to the surface upon which it rests. Furthermore, the device can be shaped to be ergonomically adapted for the operator of the device. The device may be with rounded edges, and overall organic in shape, it may have a restriction at one or more parts for the placement of fingers to hold the device. The device may be made from any suitable material and may comprise several such types of material within and without. Preferably, the device is of one or more lightweight materials.

The benefit of adapting the imaging device to be placed upon the recipient is that the person or persons administering a medical treatment have both hands free to do so. Furthermore the administering person is free from donning heavy and unhandy headgear which inhibits free sight and restricts the practitioner in his/hers whereabouts. Moreover, the advantage of the present invention is free mobility of the recipient and an easy reestablishment of the system in case the device has been moved, the recipient's skin or subcutaneous structure has moved or other similar scenarios. A further advantage of many of the embodiments of the invention such as the embodiment comprising hinged flaps of flexible material wherein the light emitting sources of the device are embedded is that optimal contact is ensured between the device and the recipient. This facilitates the imaging of the subcutaneous structures.

The recipient upon which the device can be adapted to be placed can be any living being, preferably an animal such as a mammal, and most preferably a human being. The device may be used on any part of the recipients' anatomy such as the legs, head, body or arms.

Light Sources

The present invention will comprise at least one light emitting source for the purpose of illuminating subcutaneous structures. The governing principle of the invention is the particular absorptive qualities of various subcutaneous elements, especially the absorbance by blood of specific spectral wavelengths.

It is an aspect of the present invention to provide illumination for the visualization of a selected area of body surface, hereunder lying tissue and subcutaneous structures. This can be done in a trans-illuminating mode or a reflective mode. In one embodiment of the present invention the mode of illumination is a trans-illuminating mode. In an alternative embodiment the mode is a reflective mode.

The at least one light source preferably emits light of a wavelength between 550 and 1600 nm. This spectrum includes both visible and infrared (IR) light; and sources capable of emitting either or both, singularly or combined, are provided for in an embodiment of the present invention. The visible light is preferably yellow light of a wavelength between 550 to 580 nm or 560 to 575 nm, orange light of a wavelength between 580 to 630 nm or 585 to 610 nm, red light of a wavelength between 630 to 700 nm or 640 to 665 nm. The infrared light may be near-infrared or infrared light of wavelengths between 700 and 1600 nm or more. This includes light of any wavelength therein and in any interval therein such as light of wavelengths between, but not limited to: 700 and 800 nm, 800 and 900 nm, 900 and 1000 nm, 1000 and 1100 nm, 1100 and 1200 nm, 1200 and 1300 nm, 1300 and 1400 nm, 1400 and 1500 nm, 1500 and 1600 nm, or more. Most preferably the infrared light is of a wavelength between 800 and 900 nm, such as between 810 and 890 nm, 820 and 880 nm, 830 and 870 nm, 840 and 860 nm, 845 and 855 nm or such as between 820 and 840 nm, 825 and 835 nm, such as 830 nm or 850 nm.

Preferably, the invention comprises a combination of light sources emitting yellow (550-580 nm), orange (580-630 nm), and red (630-700 nm) light. This combination provides wavelengths that are both maximally absorbed by blood and most illuminating, giving the best contrast between blood filled structures and surrounding tissue. More preferably the invention further comprises an infrared light (700 to 1000 nm) for added in light penetration through tissue.

Several sources can emit light of the above mentioned wavelengths. The light source chosen may be any physically non-threatening light source and selected from any of the non-limiting examples such as light emitting diodes (LEDs) and laser diodes (LDs), low energy IR LEDs, chemiluminescent, incandescent, laser, or fluorescent sources.

Of special interest to the present invention are various types of diodes such as, but not limited to, light emitting diodes (LEDs) and laser diodes (LDs). LEDs are semiconductor devices that emit monochromatic light of varying colors, which are generated based on the material used for the tips of the probes. Aluminium indium gallium phosphide (AlInGaP) is used for red and yellow. LEDs emitting light in the infrared spectrum are also available and may be made of Gallium Aluminium Arsenide (GaAlAs) and can be of a low energy type. LDs are likewise semiconductors, and work on the same principle as gas lasers. They function as an optical oscillator by stimulating a chain reaction of photon emission inside a tiny chamber. The most common semiconductors used in laser diodes are compounds based on gallium arsenide (750 to 900 nm in the infrared) and indium gallium arsenide phosphide (1200 to 1700 nm in the infrared).

Preferably the invention comprises light sources that are diode based such as LEDs, LDs or low energy IR LEDs. Most preferably LEDs emitting yellow, orange, red and infrared light.

The LEDs of the present invention emit light with an effect suitable for illuminating subcutaneous structures without causing discomfort in the recipient. It is a trade off between using high effect which allows better detection, but generates considerable heat, and using low effect which results in suboptimal detection, but does not burn or discomfort the recipient. Preferably, the invention comprises infrared diodes emitting light of an effect between 0.5 and 1.5 W. More preferably the infrared LED emits light of an effect between 0.9 and 1.1 W such as 1 W. Most preferably, the infrared LED emits light of a wavelength of 850 nm with an effect of 1 W.

It is an object of the present invention that the heat developed by the device, especially the LEDs is less than 50 C (degree Celsius) as measured on the surface of the skin of the recipient. Preferably the heat developed is less than 49 C, less than 48 C, 47 C, 46 C or 45 C. More preferably the heat developed by the device is less than 44 C, such as 43 C, 42 C, 41 C or 40 C. A reduction in heat development may be achieved as stated above or by pulsing the light on and off as described in the below.

The present invention comprises at least one light source. A preferred embodiment of the present invention comprises a plurality of light sources such as at least two light sources, such as four, six, ten, twelve, sixteen, twenty, twenty-four, thirty, thirty-two, thirty-six, forty, forty-four or fifty light sources, but is not limited to and may be in excess of any of these numbers of light sources.

Multiple light sources may be combined, each emitting light of the same or different colors and wavelengths. In one embodiment of the present invention all light sources will emit light of the same wavelength. In a preferred embodiment, separate sources will emit light of at least two different wavelengths, such as three or four different wavelengths.

The light sources can be arranged in any number of ways around the optics and/or camera of the device. The light sources may be arranged in a manner so that they all are oriented in the same direction. Preferably, they may be arranged at angles to each other and especially to the optics and/or camera of the device to ensure optimal illumination of the body surface and the underlying tissue and structures. Most preferably, the light sources are arranged in a manner where the angles of the individual light sources or groups of light sources relate in an equivalent way to the optics and/or camera of the device. An embodiment of the present invention may thus comprise several light sources emitting the same or at least two different wavelengths wherein the sources emitting one wavelength are placed at one angle to the optics/camera and the sources emitting light of the same or another wavelength are placed at another angle to the optics/camera of the device and so forth. The sources emitting light of the same wavelength may also be arranged at more than one angle to the optics/camera of the device.

In another embodiment of the present invention the light sources of one wavelength are arranged at different angles to each other but focus their light towards the same point, where the light sources of another wavelength likewise are arranged at different angles to each other and focus their light towards the same or a different point compared to the light sources of the first wavelength. Embodiments including light sources emitting light of a third or fourth wavelength or more different wavelengths fall within the scope of the present invention. If the angle of the light received by the camera and the camera itself is 90 degrees, then it is an aspect of the present invention that the light sources are at an angle of 30 degrees or more to each other, more preferably 20 or 15 degrees to each other, most preferably 10 to 5 degrees to each other.

As different wavelengths are either absorbed by blood, reflected by or penetrate tissue it is preferable that the different light sources emitting light having these different properties are placed at an angle to each other for optimal resolution of subcutaneous structures. Therefore, it is preferable that yellow, red and IR emitting LEDs are placed at an angle between 5 and 15 degrees of each other.

The light sources may be arranged in any configuration such as in a line, in parallel lines, squares, triangles, semi- or full circles, concentric circles or star shapes. The light sources may be thus arranged in a particular configuration around the detection device or camera, e.g. in at least one circle around the opening of the camera. They may furthermore be arranged at an angle to each other and to the camera. At least one light source may be placed in a groove or recess within the device or any straps or fastening means attached hereto, or preferably, the at least one light source may rest directly upon the body surface of the recipient. The at least one light source may be placed at a distance to the camera which can be regulated by moving the light source(s) compared to the camera/detection device or preferably, the at least one light source may be at a fixed distance to the camera/detection device.

An embodiment of the present invention includes a light guide. Said light guide is a LED or other light source emitting visible light which, by illuminating the body surface indicates to the operator of the device, exactly where to inject e.g. a hypodermic needle. The light guide is placed on the side of the device and may have a strip of material mounted in front, dividing the light beam, to further assist in locating the correct point of injection.

A further embodiment comprises a needle guide in the shape of a two-pronged fork or "V" aiding the insertion of the needle into a detected subcutaneous structure by limiting the freedom of movement to one plane. The light guide and needle guide may be present on the same embodiment of the invention.

Camera

It is an object of the present invention that it comprises means for real time visualization and true to nature rendition of a subcutaneous blood filled structure. Therefore the present invention comprises a light detecting means and a display means.

A camera like device will enable detection and recording of the light emitted from the chosen light sources. The camera like device will comprise a filtering means for the received light, a spectrally selective array type imaging device responsive to the spectrum chosen and be connected to an image forming system or display means. The detection and recording means may include but are not limited to cameras, film mediums, photocells, photodiodes, an electronic digital camera, a charge coupled device (CCD) camera, or a complementary metal oxide semiconductor (CMOS) camera.

Filters and deflectors can be used in the device as a processing means for enhancing the quality of the received light. The object may be to increase the contrast or signal to noise ratios, allow use of the system in natural or artificial lightening situations or increase the sensitivity of the signal. It is an object of the present invention that it is applicable in any setting where a medical treatment of the type described herein is likely to be administered, especially in an indoor room lit by artificial means such as fluorescent or incandescent light sources. Ambient light may thus be filtered away. It is further an object of the present invention to be applicable for localization and visualization of blood filled subcutaneous structures in recipients with varying amounts of subcutaneous fat deposits. Tissue, especially fat tissue, absorbs light very weakly, but scatters light very heavily and it is an object of the present invention to reduce the noise thus generated by filtering or deflecting means.

A deflector is a means by which the direction of the light is altered in a predetermined manner. It may be of any size or shape, having a coating or being of a material capable of reflecting light. Deflectors and their uses are generally known by those skilled in the art.

An optical filter is a device which selectively transmits light having certain properties (often, a particular range of wavelengths, that is, range of colours of light, or polarizations), while blocking the remainder. The filter is thus of an interference structure type and may be selected from but not limited to the group of bandpass (cavity, Fabry-Perot, induced transmission), low pass, high pass, band stop, polarized or tuneable filters. A novel development within the field is the use of nanotubes. Nanotubes are only a few nanometers in diameter but millimetres in length, the length-to-width ratio is thus extremely high. This ratio is of importance for filtering the light and an example of a beneficial ratio is a ratio of 200:1, but may be any ratio optimized for use in the device.

Nanotubes are based on carbon or other elements. The tubes absorb visible and IR light allowing only light travelling parallel to the tubes to reach the light detecting means. The tubes thus function as filtering devices reducing scattering dramatically. Carbon nanotubes are hexagonal lattices of carbon atoms rolled into a cylinder forming a macromolecule. The structure may be capped but is preferably uncapped and may be of the multi-walled or preferably of the single walled type. Nanotubes may be arranged in bundles or ropes or in arrays. Nanotubes in ropes or arrays function as collimators. Any type of collimator, which are devices for producing beams of parallel rays of light or other radiation, fall within the scope of the present invention. Examples of collimators include but are not limited to: ultra high resolution (UHR), high resolution (HR), general all purpose (AP), and high sensitivity (HS) collimators and silicone micromachined collimator arrays (SMCAs).

More than one filter is applicable within the present invention and these may be of the same or of different types. It is thus an object of the present invention to provide at least one filtering and/or deflecting means according to any of the herein above.

The detection of the filtered and/or deflected light is provided by an imaging device responsive to the spectrum chosen. It is an object of the present invention that the camera enabled detection system is an electronic digital camera. It is further an object of the present invention that the electronic digital camera enabled detection system comprises an array-type detector selected from the group consisting of: complementary metal oxide semiconductor (CMOS), charge coupled device (CCD) arrays and charge injection device (CID) arrays. Most preferably the presenting invention comprises complementary metal oxide semiconductor (CMOS) arrays.

A charge-coupled device (CCD) is a sensor for recording images, consisting of an integrated circuit containing an array of linked or coupled, capacitors. An image is projected by a lens on the capacitor array, causing each capacitor to accumulate an electric charge proportional to the light intensity at that location. Once the array has been exposed to the image, a control circuit causes each capacitor to transfer its contents to its neighbor. The last capacitor in the array dumps its charge into an amplifier that converts the charge into a voltage. By repeating this process, the control circuit converts the entire contents of the array to a varying voltage, which it samples, digitizes and stores in memory.

Every pixel in a charge injection device (CID) array can be individually addressed via electrical indexing of row and column electrodes; therefore charge does not transfer from site to site in the CID array as in a CCD array. Instead, a displacement current proportional to the stored signal charge is read when charge "packets" are shifted between capacitors within individually selected pixels. The displacement current is amplified, converted to a voltage, and fed to the outside world as part of a composite video signal or digitized signal. Readout is non-destructive because the charge remains intact in the pixel after the signal level has been determined. To clear the array for new frame integration, the row and column electrodes in each pixel are momentarily switched to ground releasing, or "injecting" the charge into the substrate. In this manner "blooming" or "smearing" by spill from oversaturated elements is avoided.

Complementary metal-oxide-semiconductors (CMOS) are a major class of integrated circuits. The central characteristic of the technology is that it only uses significant power when its transistors are switching between on and off states. Consequently, CMOS devices use little power and do not produce as much heat as other forms of logic. CMOS also allows a high density of logic functions on a chip.

The present invention can comprise at least one camera enabled detection system or two such detection systems, at the most three such detection systems. It is an important aspect of the present invention that at least one camera is in direct contact with the body surface of the recipient. However, the at least one camera can in an alternative embodiment be placed in a recess of the device, and thus be at a distance from the body surface of the recipient.

In embodiments where the camera is placed at a distance from the surface of the recipient the distance between these two is less than 40 mm, such as less than 35 mm, less than 30 mm, less than 25 mm. Preferably the distance between the camera and the surface of the recipient is less than 20 mm, such as 19 mm, 18 mm, 17 mm, 16 mm, 15 mm or less.

The image receiving parts of the camera, i.e. the aperture, lens and so forth, must be of a size allowing optimum visualization of the subcutaneous structures and the opening of the detection device must therefore relate to the size of such structures and be at least 5 mm in diameter, preferably 10 mm in diameter, or most preferably 20 mm in diameter. The size of the opening is not limited to any of the hereby described diameters Preferably the device comprises a CCD camera with an aperture of between 10 and 40 mm, as this size aperture allows detection of both thin, thick and branched blood vessels.

In any of the herein described embodiments the shutter closure/imaging availability of the image receiving device/camera and LED emitted light are adapted to each other in a manner whereby they can be said to pulse (the shutter opens/an image is ready for receival, the LED emits light) synchronously. The advantages hereof are less heat development as the LEDs emit heat when on, and especially the synchronous pulsing is of relevance for battery driven devices as this will prolong the life of the batteries by being less taxing energy expenditure wise.

The camera may be fitted with a wide-angle lens providing a wider angle of view, with a rectilinear projection or a non-geometric projection such as that given by a fisheye lens.

The depth of detection depends on the combination of light sources and deflector/filtering means and it is an aspect of the present invention to provide detection means up to but also in excess of a tissue depth as measured from the surface of a body of 10 mm. This detection depth is expected to be sufficient for the localization of veins and other blood filled structures in 80 to 90% of the human population. In a preferred embodiment the present invention provides means of detection of subcutaneous blood filled structures of up to 15 mm, more preferably 20 mm, even more preferably 25 mm or most preferably up to but also in excess of 30 mm. Especially for embodiments of the present invention employing a trans-illuminating mode of illuminating subcutaneous structures it is of relevance that IR light can reaching depths of approximately 150 mm. Detection depths and means to reach these of up to 40 mm, 50 mm, 60 mm, 70 mm, 80 mm, 100 mm, 120 mm and 150 mm all fall within the scope of the present invention including depths in excess of 150 mm.

Trans-Illuminating Mode

The configuration of light sources and detection device(s) or camera(s) in respect to each other and the device is an aspect of the present invention. The light detected may be light reflected or scattered by subcutaneous structures within the body of the recipient and is herein described as reflective mode. The light detected may otherwise be a combination of light that has traversed the body (part) of the recipient and reflected or scattered light; this is herein described as trans-illuminating mode.

The camera and light sources may thus be oriented in the same direction or be placed at angles to each other. If the angle between the light received by the camera and the body surface is 90 degrees and a light source placed directly opposite of the camera is at an angle of 180 degrees hereto, then in embodiments employing trans-illuminating means of visualization and detection the light sources are preferably at an angle of 180 degrees, 170 degrees or 160 degrees, relative to the at least one camera of the present invention. One such embodiment will comprise LEDs emitting yellow, orange, red and IR light placed at angles between 180 and 160 degrees relative to the light received by the camera.

Reflective Mode

In a preferred embodiment, subcutaneous structures are illuminated and visualized in a reflective mode. The light sources may be placed at a distance from the detection device or camera, the preferred light sources being LEDs. The distance can be regulated by moving the LEDs compared to the detection device/camera or be at a fixed distance hereto. Preferably, the LEDs are at a fixed distance to the detection device/camera. The LEDs will be placed upon the body surface of the recipient and rest hereon either directly or at a small distance here from. The distance may provided for by a membrane of a flexible or adaptable material, such as a silicone membrane. Depending on the distance from which the LEDs are placed from the detection device or camera the angle to same may be 90 degrees, such that the LEDs, which are arranged symmetrically, are lying on approximately the same plane i.e. at 180 degrees to each other. The angle to the detection device/camera from a given light source may be any angle between 5 degrees and 160 degrees. In one embodiment the angle may be any angle between 10 degrees and 80 degrees, such as 20 degrees, 30 degrees, 40 degrees, 50 degrees, 60 degrees or 70 degrees. In a preferred embodiment the angle between the light source and the detection device/camera is between 90 degrees and 140 degrees, more preferably between 90 degrees and 110 degrees. The light detected is the light scattered by the subcutaneous structures.

In a preferred embodiment the subcutaneous structures are illuminated in a reflective mode by at least two infrared LEDs placed symmetrically at a fixed distance from the detection device or camera at an angle between 70 degrees and 110 degrees, between 90 and 110 degrees, or between 80 and 100 degrees. The device will preferably have a detection depth of at least 10 mm in part due to the placement of the light sources relative to the camera. Most preferably, the LEDs will be placed on or embedded in hinged flaps of a flexible material ensuring optimal contact between the device, especially the LEDs, and the recipient. Due to the hinged flaps, the actual angle between the LEDs and the camera will vary depending on the curvature of the surface of the recipient. The interplay between the angle (between the LEDs and the camera) and the adaptation to the patient by any of the herein mentioned means is an important object of the present invention.

Display

It is an aspect of the present invention to provide at least one display means with the intent of rendering a true to nature rendition of the recorded real time image of illuminated subcutaneous structures. The display can be at a distance from the device itself, but preferably the display is an integrated part of the device. The display can be placed anywhere on the device, preferably the display is on a surface different from the surface resting on the recipients body surface. Most preferably the display is facing away from the body surface of the recipient, so the line of sight is perpendicular to the body surface upon which the device is placed.

The display may be any type of display known in the art. For example the display can be at least one diode, or several diodes arranged in an array such as in line with one another or in two lines parallel to each other. The display can also be of a flat panel display type such as, but not limited to, a liquid crystal display (LCD) or an organic display. The display may have a centreline printed, engraved or displayed upon it. The centreline has the purpose of aiding in aligning e.g. a hypodermic needle with the displayed image of a blood vessel. The centreline is in line with the light guide and the optional strip of material mounted in front hereof for further assistance in inserting the hypodermic needle correctly.

A liquid crystal display (LCD) is a display technology that uses rod-shaped molecules (liquid crystals) that flow like liquid and bend light. Un-energized, the crystals direct light through two polarizing filters, allowing a natural background color to show. When energized, they redirect the light to be absorbed in one of the polarizers, causing the dark appearance of crossed polarizers to show. The more the molecules are twisted, the better the contrast and viewing angle.

Organic displays also known as organic LED displays or organic electroluminescent device (OLED) are based on the discovery that light-emitting, fast switching diodes could be made from polymers as well as from semiconductors. Starting from a standard LCD glass covered with structured ITO (Indium-Tin-Oxide), the polymer materials are applied by precision ink jet printing. Using this technology, pixels of red, green, and blue material are applied. Each pixel in the display behaves in the same way as a miniature LED. After the patterned cathode has been applied via metal evaporation, the cell is sealed. Organic displays can be constructed on virtually any surface and are thinner, lighter, and more flexible in structure plus they are more power efficient.

A preferred embodiment of the present invention comprises at least one organic display means. Organic displays can display still pictures or real time video in full-color graphics. A preferred embodiment of the present invention displays real-time video.

The display can have any size compatible with the size of the device and allowing a good visualization of the subcutaneous structures. The display can be 3 by 3 cm or 4 by 4 cm, or 5 by 5 cm, or 6 by 6 cm, or it may be rectangular in shape and thus be 3 by 4 cm, or 3 by 5 cm, or 4 by 5 cm, or 4 by 6 cm, or 5 by 6 cm. These measurements are meant as examples and are not limiting for the configuration of the device.

A preferred embodiment of the invention comprises a guide light, an LCD display with a centreline, the display being about 3 by 4 cm coupled to a CCD camera receiving light from LEDs emitting yellow, orange, red and IR light.

Energy Source

The device is a handheld device that gives free mobility to the operator of the device and the recipient of a medical treatment. It is therefore an aspect of the present invention to comprise an energy source or the means i.e. at least one port, for being connected to a remote energy source. Preferably, the device comprises batteries, such as single use batteries or rechargeable batteries. In addition the device can have means for recharging the batteries such as a socket for hooking up an external wire or a cup or other holder for placing the device in for recharging. Alternatively or additionally, the device or the rechargeable batteries contained herein may be charged through a universal serial bus (USB) connection. The external wires or holders may comprise transformation means for the electric current.

The device itself may be designed for single use purposes, for use up to 100 times or for use until the batteries are discharged. The device may also be constructed for repeated use. The number of times the device is intended to be used can be reflected not only in the choice of energy source, but also in al the herein mentioned components. A device intended for single or few times usage may thus be of materials of less durability and cost compared to a device designed for continued usage.

Examples of batteries that may be used are AAA batteries or flat batteries of the type known from cellular phones or any other battery that provides a satisfactory duration of usage time of the device and total size of the device.

An embodiment of the present invention is a device of less than 100 g for use with single covers until the battery is discharged and the device is disposed of.

Communication Means

The device can comprise means for storage of images within itself in a digitalized storage means. The digital storage means can be any from the following non-exhaustive list: computer chips, universal serial bus (USB) utilities, disc devices or others. The images can subsequently be called up and be displayed upon the display of the device, to a display separate from the device, or be transferred to an external storage medium or printer. The exchange of images, stills, video or other information gathered, from the device and to any surrounding media can be done by USB means, moveable disc, or wireless communication means such as Ethernet, blue tooth, IR ports or other wireless computerized communication means. This includes that the device comprises at least one assembly for communication purposes, such as ports for plug-in devices, ports for wire transfer or means for wireless communication. A preferred embodiment comprises at least one wireless communication means. An alternative embodiment of the present invention comprises a thermal paper printing means.

Any technique known in the art that can accomplish any of the above mentioned functions fall within the scope of the present invention. Especially in regards to the administration of a medical treatment, it is an aspect of the present invention to provide means for the storage of rendered images in any form, of subcutaneous structures prior to, during and after the administration of the medical treatment. In a preferred embodiment this is accomplished by the device comprising a USB port which simultaneously allows for recharging the device.

Alternative Embodiments

All the herein above described embodiments are comprised within the scope of the present invention, which also encompasses several alternative embodiments as described hereafter.

An embodiment of the present invention comprises the display of a rendered image in three dimensions (3D). This can be accomplished by the use of cameras, image processing means and displays as are known in the art. In a preferred embodiment the present invention comprises at least two cameras arranged at an angle to one another with the intent of providing a 3D image.

An alternative embodiment of the present invention includes a system to gather and relay sound. The intent of the device according to the present invention is to localize subcutaneous structures, especially veins and arteries. Veins and arteries pump blood under pressure, and arteries inherently pump with a higher pressure than veins. This fact can be employed in the distinction between venous and arterial structures and can be relayed to the operator of the device e.g. a by both visual and audible means. The pulse can thus be made audible to the operator of the device.

A further aid in the process of detecting and visualizing subcutaneous structures can be the addition of an ultrasound scanning function to an embodiment of the present invention. An ultrasound emitting and receiving device can be used in an embodiment of the present invention with the intent of localizing and visualizing subcutaneous blood filled structures. In an alternative embodiment, the ultrasound devices are combined with the light detection system of the herein described embodiment of the present invention.

It is understood that modification to the invention may be made as might occur to one having skill in the field of the invention within the scope of the herein described and claimed embodiments. All the embodiments contemplated hereunder that achieve the objects of the invention have therefore not been shown in complete detail. Other embodiments may be developed without departing from the spirit of the invention or the scope of the herein described embodiments and appended claims.

Subcutaneous Structures

Subcutaneous structures that can be visualized with the device are any structures which absorb light of the wavelength emitted from the chosen light sources. It is an object of the invention to provide real time, true to nature images of haemoglobin filled structures. Haemoglobin filled structures include blood vessel such as veins, arteries and capillaries or blood filled spaces such as haematomas occurring during or found after a haemorrhage. Furthermore, cancers, tumors, infected areas or other abnormal structures which are vascularised or blood enriched will be visualized.

It is an aspect of the present invention to provide means for the detection of blood vessels especially veins and arteries, most especially veins. In an embodiment of the present invention means are provided by which it is possible to distinguish between veins and arteries. This can be done due to the inherent difference in pressure between veins and arteries and the clear presence of a pulse in an artery.

Foreign objects will likewise be visualized if they absorb or reflect the light emitted from the present invention. For example the tip of a hypodermic needle will be visible together with any other subcutaneous structures present. This means that the precise location of the tip of the needle compared to for example a blood vessel such as a vein or artery can be seen with the herein described device. This is extremely useful for the administration of several types of medical treatments in that the tip of a hypodermic needle will be visible simultaneously with the blood vessel ensuring that the tip is inserted into the vessel and the fluid in the hypodermic needle or drip bag is administered into the blood stream.

Medical Treatment

The present invention greatly facilitates the administration of several types of medical treatments. Any type of medical treatment that requires the visualization of subcutaneous structures will benefit from the use of this device. This includes the simple visualization of subcutaneous structures, i.e. for determining the presence and extent of a haemorrhage, infection, varicose vein or other.

Treatments potentially painful for the recipient in that they require injection or other types of incisions into the surface of the recipient can be performed accurately and need not be repeated at the recipients risk or discomfort when using the present invention. Especially injections into blood vessels such as veins for the administration or extraction of fluids will be facilitated. Other treatments that will be facilitated include placing of drips, sampling of blood, placement of probes and insertion of catheters for example peripherally inserted central venous catheters (picc lines). Prior to administering antibiotics, cytotoxic drugs such as a chemotherapeutic agent or other to the recipient it is common procedure to flush the vein with an amount of saline water to ensure that the cannula/catheter is correctly placed inside the vein. A large amount of saline water may be required to ensure this. The device of the present invention alleviates the need for flushing with large amounts of saline water (or other fluids) as the displacement of the blood inside the vein by even small amounts of saline water is visible, as is the haemorrhaging that may be associated with a false puncture of the vein. In this manner, as in any of the above described, the "1st attempt" peripheral cannulation success rate is greatly improved. Likewise, the device may be used to provide ongoing verification of the correct placement of a cannula/catheter, such as in patients receiving any type of fluid from an intravenous (IV) drop or the like. Thus, it is an embodiment of the present invention to provide a device and a method of using said device wherein said device is capable of improving the success rate of an initial cannulation attempt and/or capable of ensuring/verifying the correct placement of any intravenous device at any point in time while a cannula/catheter or other is inserted into the recipient.

The facility with which medical treatments can be administered aided by the device of the present invention will furthermore be an economic incentive for its production. This is due to several factors including the time saved when only one insertion is required for performing a medical treatment. It thus alleviates time spent on unsuccessful insertions, waiting for a second medical practitioner to repeat the attempts, and any delays in performing subsequent medical treatments. Furthermore the cost of repeatedly disposing medical instruments due to potential contamination after erroneous insertion into the recipient will be reduced as will the number of procedures that may follow due to the administration of erroneous treatments.

Biometrics

The pattern of subcutaneous blood filled structures within an individual is highly unique and can therefore be used as a personal identification means. Furthermore, said pattern, being subcutaneous, is extremely difficult to alter or duplicate and is therefore a biological trait ideally suited for authentication of personal identity. Biometrics is the science and technology of authentication by measuring an individuals physiological or behavioural features. The use of biometrics is a rapidly expanding within all areas where authentication of personal identity is of relevance for security reasons, such as the finance, defence, and government sectors. The present invention provides means for rapid identification of individuals based on their subcutaneous blood filled structures. It is an object of the present invention to provide a means for immediate visual identification of individuals based on their subcutaneous blood filled structures. A preferred embodiment of the present invention is a small, portable, handheld device, in contact by any means known in the art to storage and communication means for relaying, comparing and identifying images of subcutaneous blood filled structures.

Methods

The invention furthermore relates to the use of the herein above described embodiments of the device. The use primarily relates to the visualization of subcutaneous structures in a body, said subcutaneous structures mainly being blood filled vessels. The use of the device according to any of the herein described specifications especially the specification of the device being adapted to be placed directly upon the surface of the recipient comprises the steps of: 1) emitting light onto a selected area of body surface, hereunder lying tissue and subcutaneous structures, 2) detecting the reflected light by camera enabled detecting means and recording an image of illuminated subcutaneous structures and 3) displaying the real time image of true to nature illuminated subcutaneous structures. The device is especially adapted for localizing blood vessels prior to and during injection of vessels with the tip of a hypodermic needle or other medical instrument and therefore the preferred use of the device includes these steps.

The method of visualizing subcutaneous structures in a body with a device being adapted to be placed directly upon the recipient, comprising the steps of: 1) emitting light onto a selected area of body surface, hereunder lying tissue and subcutaneous structures, 2) detecting the reflected light by camera enabled detecting means and recording an image of illuminated subcutaneous structures and 3) displaying the real time image of illuminated subcutaneous structures. Preferably the device is of any of the herein described embodiments and more preferably the method is applied prior to and during the injection the tip of a hypodermic needle or other medical instrument into said subcutaneous structures such as blood vessels.

The method of visualizing subcutaneous structures in a body with a device being adapted to be placed directly upon the recipient, comprising the steps of: 1) emitting light onto a selected area of body surface, hereunder lying tissue and subcutaneous structures, 2) detecting the reflected light by camera enabled detecting means and recording an image of illuminated subcutaneous structures, 3) displaying the real time image of illuminated subcutaneous structures and 4) by communication, storage and processing means comparing said image with stored images. Preferably the device is of any of the herein described embodiments and more preferably the method is used to authenticate the identity of an individual.

DETAILED DESCRIPTION OF THE DRAWINGS

FIG. 1:

Illustrates a preferred embodiment of the invention employing a reflective mode of illuminating and visualizing subcutaneous blood filled structures. The device is shown at four different angles. 1a: View of one of the two sides of the device that will be perpendicular to the arm 8 or vein 11 of the patient. The device is adapted to be placed upon the recipient by the concave shape of the device which fits the convex surface of the recipient. The top of the device 1 facing away from the recipient has the display 4, inserted. The bottom of the device 2 is a lid, and rests upon the surface of the recipient. This bottom lid 2, is made of a light transparent material and covers the light emitting diodes (LEDs) 7, and other components. The side 3 of the device brings together the top 1, and the bottom lid 2, making up the housing of the device wherein LEDs 7, camera 15, batteries 16 and more are comprised. There is a light guide 5 in the bottom lid 2, of the device. The light guide 5 is a LED emitting visible light, which shines onto the surface of the recipient to aid in the insertion of e.g. a hypodermic needle into the subcutaneous structure visualized upon the display 4. The light guide 5 has a strip 6 of material mounted in front to further facilitate the insertion of e.g. a hypodermic needle. 1b: View of the one of the two sides of the device that will be parallel to the arm of the recipient, in which the on/off switch 9 is placed. The switch 9 is placed on this side for easy manipulation—turning the device on and off—by the operator. Due to the concave shape of the device, the display 4 is visible from this side. 1c: Slightly elevated corner view of the device illustrating the ergonomic curvature, light guide 5, light guide strip 6 and display 4 of the device. The display 4 is a liquid crystal display (LCD) shaped to follow the curvature of the device. 1d: View of the top 1 of the device into which the display 4 is inserted. The display 4 is at least 3 by 4 cm and has a centreline 10 marked upon it. The centreline 10 is in line with the light guide 5 and the light guide strip 6 on the side of the device depicted in 1a. The centreline 10 runs across the display upon which the subcutaneous structures are visualized, here a vein 11. By aligning the centreline 10 with the real time image of the vein 11 as displayed on the display 4 the guide light 5 shines upon the body surface of the recipient exactly above the vein 11. The strip 6 further pinpoints the exact place to insert e.g. a hypodermic needle.

FIG. 2:

Illustrates a preferred embodiment of the invention employing a trans-illuminating mode of illuminating and visualizing subcutaneous blood filled structures. The device is shown at four different angles. 2a: View of one of the two sides of the device that will be perpendicular to the arm 8 or vein 11 of the recipient. This embodiment comprises two halves: the housing 18 comprising the camera 15, display 4, batteries 16, and electronics 19, and the back light 17 comprising the LEDs 7 that will illuminate the subcutaneous structures. A strap 14 connects the two halves and keeps the device securely mounted on the recipient. The back light 17 is made up of the back light top 12, and the back light bottom 13 from which the LEDs 7 protrude. The bottom 2 of the housing 18 is as described for the previous embodiment a light transparent lid allowing the unabsorbed light access to the camera 15, which lies behind the lid together with the other internal components. As with the embodiment employing the reflective mode of illumination, this embodiment of the device is adapted to be placed upon the recipient by the concave shape of both halves of the device, which fits the convex surface of the recipient. This embodiment also comprises a light guide 5 and light guide strip 6 as previously described. 2b: View of the one of the two sides of the device that will be parallel to the arm of the recipient, in which the above described on/off switch 9 is placed. The switch 9 is placed in the housing 18 of the device. 2c: Slightly elevated corner view of the device illustrating the ergonomic curvature, light guide 5, light guide strip 6 and display 4 of the device. Again the display 4 is a liquid crystal display (LCD) shaped to follow the curvature of the device. From this angle, the array of LEDs 7 is visible. The array comprises LEDs 7 emitting yellow, red, orange and infrared light. As the LEDs 7 are placed in the bottom 13 of the concave back light 17, the LEDs 7 are row by row at an angle to one another. The LEDs 7 emit light towards the same point, this being the camera aperture 15 placed within the housing 18. The number of LEDs 7 may be as shown or the array may comprise additional LEDs 7. 2d: View of the top 1 of the device into which the display 4 is inserted. The display 4, centreline 10 and vein 11 are as described above. Furthermore, the strap 14 is visible from this angle.

FIG. 3:

Illustrates the underside and some of the internal components of a preferred embodiment of the invention employing a reflective mode of illuminating and visualizing subcutaneous blood filled structures. 3a: View of the underside of the device with the light transparent bottom lid 2 in place. 3b: Same view with the bottom lid 2 removed. The thus visible internal components include batteries 16, LEDs 7, camera 15 and further house the electronics 19 of the device. The LEDs 7 emit yellow, red, orange and infrared light and are placed at angles to one another. The device may comprise the number of LEDs 7 shown or preferably more LEDs 7. The camera 15 is placed at the centre of the device to confer the most intuitive use of the device. The camera 15 is a ccd camera and comprises an optical filter, preferably a filter composed of nanotubes in arrays or other collimator type filters. The preferred embodiment of the invention employing a trans-illuminating mode of illuminating and visualizing subcutaneous blood filled structures comprises with the exception of the LEDs 7, the same internal components in the housing 18 as can be seen in FIG. 3b.

FIG. 4:

Illustrates a preferred embodiment of the invention employing a reflective mode of illuminating and visualizing subcutaneous blood filled structures, this embodiment comprising straps. The device is shown at four different angles. 4a: View of one of the two sides of the device that will be perpendicular to the arm 8 or vein 11 of the recipient. This embodiment comprises two halves: the housing 18 comprising the camera 15, display 4, batteries 16, and electronics 19, and a pivot flap 20 comprising the LEDs 7 that will illuminate the subcutaneous structures. The LEDs 7 are in this embodiment embedded in a silicone block visible from the inside as well as outside of the present embodiment. The LEDs 7 are infrared LEDs of high effect and are via the silicone casing placed at a small distance from the surface of the recipient. A strap 14 connects the two pivot flaps 20 and keeps the device securely mounted on the recipient. The bottom 2 of the housing 18 is as described for the previous embodiment a light transparent lid allowing the reflected light access to the camera 15, which lies behind the lid together with the other internal components. This embodiment of the device is arched and rests by the pivot joints 22 on the arm of the recipient allowing for the insertion of the hypodermic needle under the device, whereby the inserted needle can be visualized on the display 4. 4b: View of the one of the two sides of the device that will be parallel to the arm of the recipient, in which the above described on/off switch 9 is placed. The switch 9 is placed in the housing 18 of the device. 4c: Slightly elevated corner view of the device illustrating the display 4 which again is a liquid crystal display (LCD). The LEDs 7 emit light towards the same point inside the recipient. The number of LEDs 7 may be two as shown with one LED on either side of the recipient's arm, alternatively additional LEDs may be added. 4d: View of the top 1 of the device into which the display 4 is inserted. The display 4, centreline 10 and vein 11 are as described above. The display also comprises an indicator 21 indicating the status of the battery powering the device. Furthermore, the pivot flap 20 and LED 7 comprising blocks are visible from this angle.

FIG. 5:

Illustrates a preferred embodiment of the invention employing a reflective mode of illuminating and visualizing subcutaneous blood filled structures, this embodiment comprising symmetrical light guides. The device is shown at four different angles. 5a: View of one of the two sides of the device that will be perpendicular to the arm 8 of the recipient. This embodiment comprises the housing 18 with the camera 15, display 4, batteries 16, and electronics 19, and a pivot flap 20 comprising the embedded LEDs 7 that will illuminate the subcutaneous structures. The LEDs 7 are also in this embodiment embedded in a silicone block. The LEDs 7 are infrared LEDs of high effect and are via the silicone casing placed at a small distance from the surface of the recipient. This embodiment of the device rests directly on the arm of the recipient. One of the two hooded light guides 23 is visible at this angle. 5b: View of the one of the two sides of the device that will be parallel to the arm of the recipient, showing the pivot flap 20, the embedded LEDs 7 and the switch 9. 5c: Slightly elevated corner view of the device illustrating the display 4 which again is a liquid crystal display (LCD). The LEDs 7 emit light towards the same point inside the recipient. 5d: View of the top 1 of the device into which the display 4 is inserted. The display 4, centreline 10 and vein 11 are as described above. The display also comprises an indicator 21 indicating the status of the battery powering the device. Furthermore, the pivot strap 20 and LED 7 comprising blocks are visible from this angle. The two hooded light guides 23 are visible from this angle. The purpose of having two is to ensure that the device can be used to assist in the insertion of a needle at both ends of the device.

FIG. 6:

Illustrates the underside and some of the internal components of a preferred embodiment of the invention employing a reflective mode of illuminating and visualizing subcutaneous blood filled structures, this embodiment comprising symmetrical light guides. 6a: View of the underside of the device with the light transparent bottom lid 2 in place. The pivot joints 22, pivot flaps 20, hooded light guide 23 and LEDs 7 embedded in silicone are furthermore visible. 6b: Same view with the bottom lid 2 removed. The thus visible internal components include batteries 16, and camera 15 and further house the electronics 19 of the device. The camera 15 is placed at the centre of the device again to confer the most intuitive use of the device. The camera 15 is a ccd camera and comprises an optical filter, and a wide angle lens. The aperture of the camera 15 is between 10 and 40 mm in diameter to allow for the real time imaging of thick, thin and branched subcutaneous blood vessels such as veins 11.

FIG. 7:

Illustrates the underside and some of the internal components of a preferred embodiment of the invention employing a reflective mode of illuminating and visualizing subcutaneous blood filled structures, this embodiment comprising straps. 7a: View of the underside of the device with the light transparent bottom lid 2 in place. The pivot joints 22, pivot straps 20, connecting straps 14 and LED 7 embedded silicone blocks are furthermore visible. 7b: Same view with the bottom lid 2 removed. The thus visible internal components include batteries 16, and camera 15 and further house the electronics 19 of the device. The camera 15 is placed at the centre of the device again to confer the most intuitive use of the device. The camera 15 is a ccd camera and comprises an optical filter, and a wide angle lens. The aperture of the camera 15 is between 10 and 40 mm in diameter to allow for the real time imaging of thick, thin and branched subcutaneous blood vessels such as veins 11.

The invention claimed is:

1. An imaging device designed with the intent of visualizing subcutaneous structures in a body of a recipient, comprising:
   a) at least one light emitting source illuminating a selected area of body surface, underlying tissue and subcutaneous structures,
   b) at least one camera enabled detection system recording an image of said illuminated subcutaneous structures,
   c) at least one display means rendering a recorded image of the illuminated subcutaneous structures, wherein the display is an integrated part of the device, and wherein said display is on a surface of the device facing away from the body surface of the recipient
   d) said device being adapted to be placed directly upon the recipient,
      wherein said at least one light source emits light in an angle to the camera enabled detection system, said angle being between 5 degrees and 160 degrees,
   e) wherein said at least one light source is embedded in a strap or a hinged flap attached to said device, and/or said at least one light source rests at a distance from the body surface, wherein said distance is provided for by a membrane, and/or wherein the at least one light source provides for trans-illumination.

2. The device according to claim 1, wherein the device is fastened to the recipient by a fastening means.

3. The device according to claim 1, where the subcutaneous structures are blood vessels.

4. The device according to claim 1, where the subcutaneous structures are veins.

5. The device according to claim 1, where the subcutaneous structures are veins wherein a hypodermic needle is inserted.

6. The device according to claim 1, wherein the light source illuminates the body surface in a reflective mode.

7. The device according to claim 1, wherein the light source illuminates the body surface in a trans-illuminating mode.

8. The device according to claim 1, wherein at least one light source is a light source emitting visible light.

9. The device according to claim 1, wherein at least one light source emits yellow, orange or red light.

10. The device according to claim 1, wherein at least one light source is an infrared light emitting source.

11. The device according to claim 1, wherein the light source is selected from the group of consisting of light emitting diodes (LEDs) and laser diodes (LDs).

12. The device according to claim 1, wherein the light sources are arranged in at least one angle to the camera.

13. The device according to claim 1, wherein at least one light source is in direct contact with the body surface of the recipient.

14. The device according to claim 1, wherein the device comprises a means for filtering or deflecting the reflected light.

15. The device according to claim 1, wherein the camera enabled detection system is an electronic digital camera.

16. The device according to claim 1, wherein at least one display is placed facing away from the body surface of the recipient.

17. The device according to claim 1, wherein all the components of the device are comprised within a frame no larger than 350 cm$^3$.

18. The device according to claim 1, wherein the positioning of at least two cameras allow for the visualization of subcutaneous structures in three dimensions.

19. The device according to claim 1, wherein the device comprises an ultrasound emitting source and an ultrasound detection system.

20. The device according to claim 1, wherein the device comprises a least one port for a remote power supply.

21. The device according to claim 1, wherein the device comprises at least one digital storage means.

22. The device according to claim 1, wherein the device comprises at least one assembly for communication purposes selected from the group of: ports for plug-in devices, ports for wire transfer, means for wireless communication.

23. The device according to claim 1, wherein the device comprises at least one wireless communication means.

24. The device according to claim 1, wherein the recipient, the device is adapted to be placed upon, is a human being.

25. A method of visualizing subcutaneous structures in a body, comprising the steps of:
   a) emitting light onto a selected area of body surface, hereunder lying tissue and subcutaneous structures,
   b) detecting the reflected or transilluminated light by camera enabled detecting means and recording an image of illuminated subcutaneous structures,
   c) displaying the image of illuminated subcutaneous structures,
   d) wherein these step are performed with a device as defined in claim 1 being adapted to be placed directly upon the recipient.

26. The method according to claim 25, wherein a device as defined in claim 1 is used for visualizing subcutaneous blood vessels prior to and during injecting the tip of a hypodermic needle into said vessels.

27. The method according to claim 25, wherein the device as defined in claim 1 is used for visualizing subcutaneous blood filled structures for the purpose of identifying an individual thereby.

* * * * *